United States Patent
Soryal et al.

(10) Patent No.: US 12,406,531 B2
(45) Date of Patent: Sep. 2, 2025

(54) VIRTUAL REALITY USER HEALTH MONITORING

(71) Applicant: AT&T Intellectual Property I, L.P., Atlanta, GA (US)

(72) Inventors: Joseph Soryal, Glendale, NY (US); Shawn Rajguru, Summit, NJ (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 608 days.

(21) Appl. No.: 17/737,473

(22) Filed: May 5, 2022

(65) Prior Publication Data
US 2023/0360442 A1    Nov. 9, 2023

(51) Int. Cl.
| | |
|---|---|
| *G08B 21/02* | (2006.01) |
| *A61B 5/00* | (2006.01) |
| *A61B 5/11* | (2006.01) |
| *A61B 5/16* | (2006.01) |
| *G06V 40/20* | (2022.01) |

(52) U.S. Cl.
CPC .............. *G06V 40/23* (2022.01); *A61B 5/112* (2013.01); *A61B 5/162* (2013.01); *A61B 5/4561* (2013.01); *A61B 5/4803* (2013.01); *A61B 5/7264* (2013.01); *A61B 5/7282* (2013.01); *A61B 5/744* (2013.01); *G08B 21/02* (2013.01)

(58) Field of Classification Search
CPC ...... G06V 40/23; G06V 10/764; G06V 40/20; A61B 5/112; A61B 5/162; A61B 5/4561; A61B 5/4803; A61B 5/7264; A61B 5/7282; A61B 5/744; A61B 5/1118; A61B 5/7275; G08B 21/02

USPC ......................................................... 382/128
See application file for complete search history.

(56) References Cited

U.S. PATENT DOCUMENTS

| | | | |
|---|---|---|---|
| 2010/0042364 A1 | 2/2010 | Nakamura et al. | |
| 2012/0229634 A1* | 9/2012 | Laett ...................... | G16H 40/67 348/143 |
| 2018/0193589 A1* | 7/2018 | McLaughlin .......... | G06F 3/016 |
| 2019/0095775 A1* | 3/2019 | Lembersky ............ | G06N 3/006 |

(Continued)

FOREIGN PATENT DOCUMENTS

CN    106901692 A  *  6/2017

OTHER PUBLICATIONS

Chang, Z., et al., "Accurate detection of cerebellar smooth pursuit eye movement abnormalities via mobile phone video and machine learning", Scientific Reports, Oct. 29, 2020, downloaded from https://www.nature.com/articles/s41598-020-75661-x, 10 pages.

(Continued)

*Primary Examiner* — Charlotte M Baker

(57) ABSTRACT

A processing system including at least one processor may obtain a data feed of a region of a virtual environment associated with a virtual representation of a user within the virtual environment and extract behavioral data of the virtual representation of the user from the data feed. The processing system may further detect at least one health anomaly related to a physical condition of the user from the behavioral data via at least one first detection model for detecting the at least one health anomaly and generate an alert in response to the detecting of the at least one health anomaly that is related to the physical condition of the user.

20 Claims, 4 Drawing Sheets

(56) References Cited

U.S. PATENT DOCUMENTS

2023/0086248 A1* 3/2023 Puyol .................... G06F 9/451
  715/848

OTHER PUBLICATIONS

Oliveira, J., et al., "Computer-aided autism diagnosis based on visual attention models using eye tracking", Scientific Reports, May 12, 2021, downloaded from https://www.nature.com/articles/s41598-021-89023-8, 11 pages.

Nam, SH, et al., "Biological-Signal-Based User-Interface System for Virtual-Reality Applications for Healthcare", Hindawi, Journal of Sensors, vol. 2018, Article ID 9054758, 11 pages.

* cited by examiner

VIRTUAL REALITY USER HEALTH MONITORING

The present disclosure relates generally to virtual reality devices and systems, and more particularly to methods, computer-readable media, and apparatuses for detecting via at least one detection model at least one health anomaly related to a physical condition of a user from behavioral data of a representation of user that is extracted from a data feed of a region of a virtual environment.

BACKGROUND

Mixed reality (MR), augmented reality (AR), virtual reality (VR), or video-based communication sessions, such as calls, video game environments, group hangouts, and the like may include multiple participants simultaneously experiencing a shared virtual environment. User access devices may include VR headsets, AR headsets, smart glasses, or the like. A user access device may obtain a data feed of a virtual environment simultaneous with other user access devices and may render an experience for a user from a given perspective of that user within the virtual environment. The virtual environment may include fixed or substantially fixed features, e.g., ground, floors, walls, terrain, etc. and movable and/or temporary features, e.g., representations of other users, virtual objects that are moveable within the space of the virtual environment, and so forth.

SUMMARY

In one example, the present disclosure describes a method, computer-readable medium, and apparatus for detecting via at least one detection model at least one health anomaly related to a physical condition of a user from behavioral data of a virtual representation of the user that is extracted from a data feed of a region of a virtual environment. For instance, in one example, a processing system including at least one processor may obtain a data feed of a region of a virtual environment associated with a virtual representation of a user within the virtual environment and extract behavioral data of the virtual representation of the user from the data feed. The processing system may further detect at least one health anomaly related to a physical condition of the user from the behavioral data via at least one first detection model for detecting the at least one health anomaly and generate an alert in response to the detecting of the at least one health anomaly that is related to the physical condition of the user.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
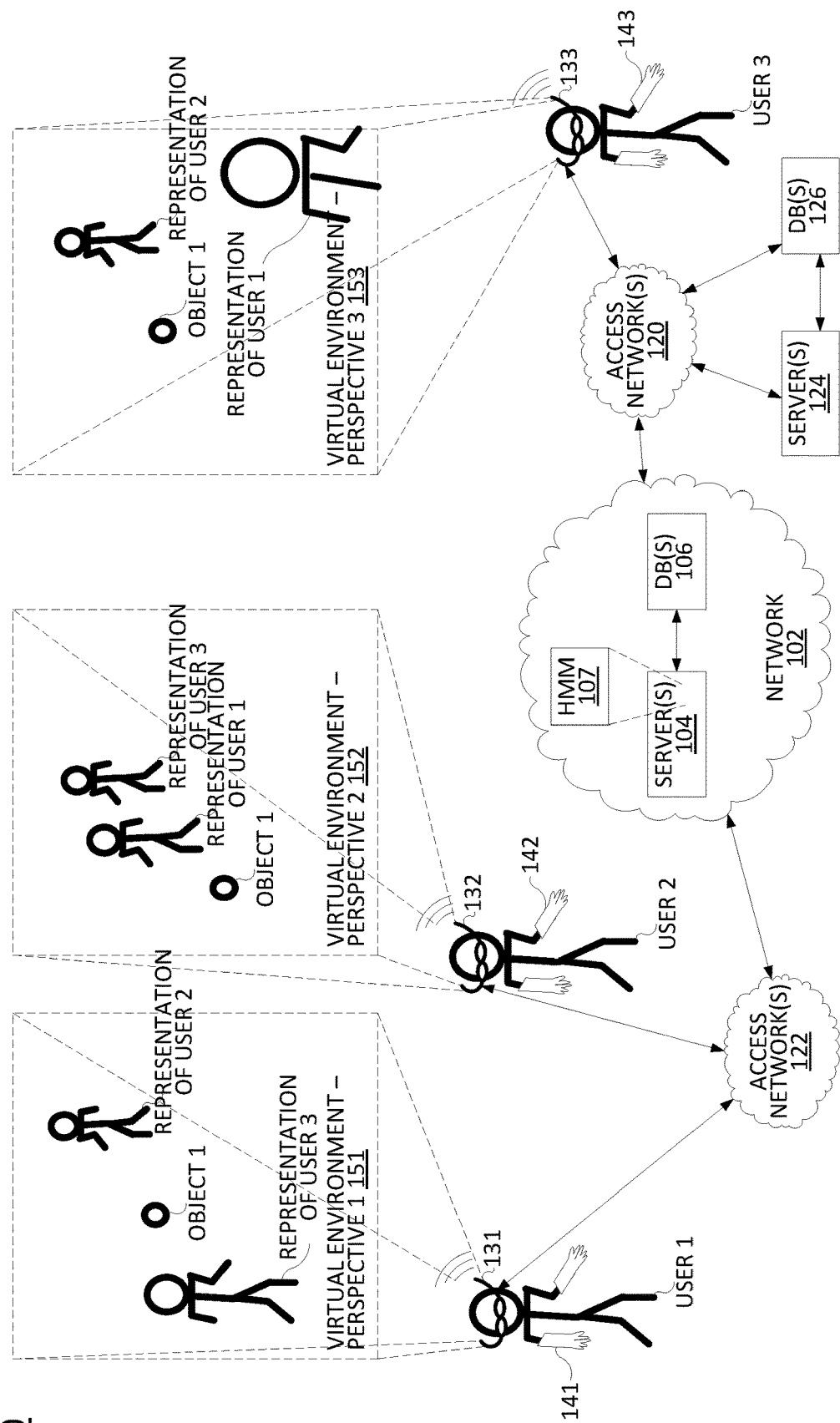
FIG. 1 illustrates an example system related to the present disclosure.

Examples of the present disclosure describe methods, computer-readable media, and apparatuses for detecting via at least one detection model at least one health anomaly related to a physical condition of a user from behavioral data of a virtual representation of the user that is extracted from a data feed of a region of a virtual environment. In particular, examples of the present disclosure provide a monitoring system that tracks the health of users in a virtual environment (e.g., a VR environment, which may include an augmented reality (AR) environment, an extended reality or mixed reality (MR) environment, and/or a "metaverse" type environment) and generates physical/real-world warnings, or alerts for detected potential health issues. Notably, users may increasingly spend more and more hours on social media each week. This trend may continue and may even worsen for VR experiences as the "metaverse" concept continues to be explored and developed. Some users may be engaged in virtual experiences for hours or even days without proper food, drink, or rest. In addition, some users may exhibit health issues over time (such as slower reactions, missing targets in a game, etc.) or may suffer more acute health issues (e.g., dehydration, blurry visions, headaches, speech impediments, etc.). In accordance with the present disclosure, such health issues may be detected via observation and tracking of behavioral data relating to a user's virtual representation within a virtual environment (such as the user's avatar, or the like).

In one example, the present disclosure may comprise a health monitoring module (HMM) that may function as one or more virtual sensor devices (e.g., a virtual camera and/or a virtual microphone) "inside" the virtual environment. For instance, the HMM may take a data feed from the virtual environment (e.g., visual and/or audio data) and may perform analytical processing relating to behavioral data of virtual user representations (e.g., avatars) to track users' health. In one example, each user may have a personalized HMM. For instance, respective HMMs may be deployed in respective user devices that are used to access a virtual environment (goggles, computer, camera, etc.). In one example, HMMs are connected to one or more servers for hosting the virtual environment, e.g., for storing data of a virtual environment, and for aggregating and disseminating data feed(s) for user experiences.

In one example, an HMM may track a user's health history in terms of behavioral data of the virtual representation of the user in the virtual environment. For instance, the behavioral data may include data pertaining to the walking speed, running speed, gait, posture, or the like of the virtual representation of the user. Similarly, such behavioral data may alternatively or additionally include speed, reaction timing, and/or accuracy of one or more types of motion of the virtual representation of the user. For instance, this may relate to an external stimulus, such as another virtual user representation speaking or otherwise interacting with the virtual representation of the user, tracking, catching, throwing, blocking, etc. of a movable virtual object, operating a virtual vehicle on a virtual path or around virtual obstacles, and so forth. In one example, the behavioral data may more generally be tracked for indicators of lack of energy, being immersed in the virtual environment for a long time without a break, and so forth.

In one example, the HMM may similarly track the way a virtual representation of a user talks or otherwise generates audible utterances. For instance, speech/utterances of the virtual representation of the user in the virtual environment may represent/mimic how the user talks in the physical/real world, but may be different from the user's "true voice." For instance, the speech/utterances of the virtual representation of the user in the virtual environment may be generated by processing speech/utterances in the user's true voice as recorded by a microphone (e.g., a real/physical microphone) through an audio transformation process to alter the user's voice, such as translating and generating speech in a different language, changing the pitch, depth, volume, or other features of the user true speech/utterances, and so forth. For instance, sudden difficulty talking could indicate a potential stroke. However, it should be understood that the HMM of the present disclosure specifically tracks a user's health and detects health issues (e.g., health anomalies) in accordance with the data feed of the virtual environment, and more specifically, in one example, the audio data relating to the speech/utterances of the virtual representation (e.g., an avatar) of the user in the virtual environment rather than the actual speech/utterances of the user in the physical/real world.

In one example, once an HMM observes a potential health issue for a user, the HMM may first alert the user in the virtual environment, such as via a red flashing light, a siren, a text box that is displayed in a prominent part of the user's field of vision, etc. Secondly, the HMM may sound an alarm on the user's mobile phone, may notify a medical service provider (e.g., a doctor, hospital, emergency medical service, etc.), may notify a caregiver, and so on. In addition, in one example, the HMM may be connected to and synced with one or more health applications (apps), health monitoring devices (such as a fitness band, smart watch, heart rate monitor, or similar internet-of-things (IoT) health monitoring device, and implant device, and so on), and so forth. In one example, the HMM may be connected to a data repository for the user's health data. For instance, the HMM, or another entity having access to the data repository may correlate the user's health data with any health events and/or alerts surfaced during the use of the virtual environment, e.g., to confirm the health event/alert has likely occurred. The HMM may make intelligent decisions either locally and/or via consulting one or more servers that aggregate(s) the user experiences of the virtual environment. These and other aspects of the present disclosure are discussed in greater detail below in connection with the examples of FIGS. 1-4.

To further aid in understanding the present disclosure, FIG. 1 illustrates an example system 100 in which examples of the present disclosure may operate. The system 100 may include any one or more types of communication networks, such as a traditional circuit switched network (e.g., a public switched telephone network (PSTN)) or a packet network such as an Internet Protocol (IP) network (e.g., an IP Multimedia Subsystem (IMS) network), an asynchronous transfer mode (ATM) network, a wireless network, a cellular network (e.g., in accordance with 3G, 4G/long term evolution (LTE), 5G, etc.), and the like related to the current disclosure. It should be noted that an IP network is broadly defined as a network that uses Internet Protocol to exchange data packets. Additional example IP networks include Voice over IP (VoIP) networks, Service over IP (SoIP) networks, and the like.

In one example, the system 100 may comprise a network 102, e.g., a telecommunication service provider network, a core network, an enterprise network comprising infrastructure for computing and communications services of a business, an educational institution, a governmental service, or other enterprises. The network 102 may be in communication with one or more access networks 120 and 122, and the Internet (not shown). In one example, network 102 may combine core network components of a cellular network with components of a triple play service network; where triple-play services include telephone services, Internet services and television services to subscribers. For example, network 102 may functionally comprise a fixed mobile convergence (FMC) network, e.g., an IP Multimedia Subsystem (IMS) network. In addition, network 102 may functionally comprise a telephony network, e.g., an Internet Protocol/Multi-Protocol Label Switching (IP/MPLS) backbone network utilizing Session Initiation Protocol (SIP) for circuit-switched and Voice over Internet Protocol (VoIP) telephony services. Network 102 may further comprise a broadcast television network, e.g., a traditional cable provider network or an Internet Protocol Television (IPTV) network, as well as an Internet Service Provider (ISP) network. In one example, network 102 may include a plurality of television (TV) servers (e.g., a broadcast server, a cable head-end), a plurality of content servers, an advertising server (AS), an interactive TV/video on demand (VoD) server, and so forth.

Figure 3:
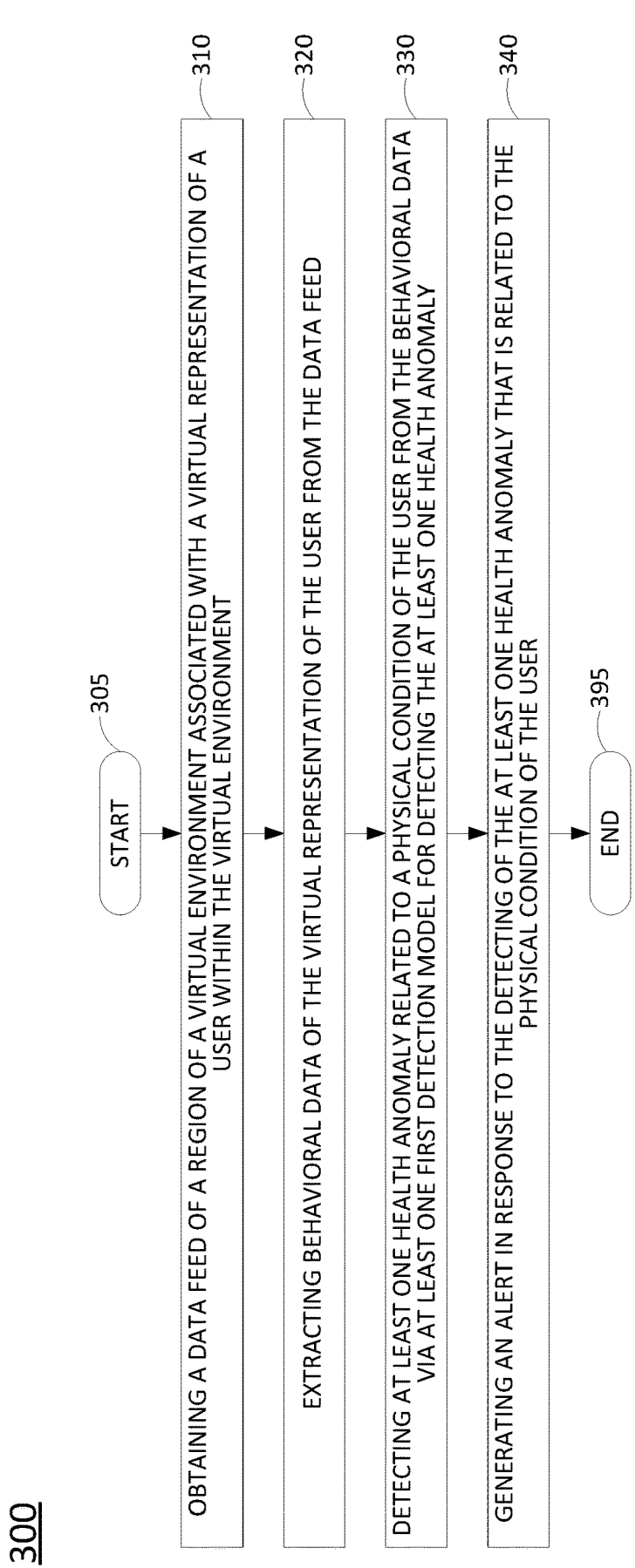
FIG. 3 illustrates a flowchart of an example method for detecting via at least one detection model at least one health anomaly related to a physical condition of a user from behavioral data of a virtual representation of the user that is extracted from a data feed of a region of a virtual environment.
Figure 4:
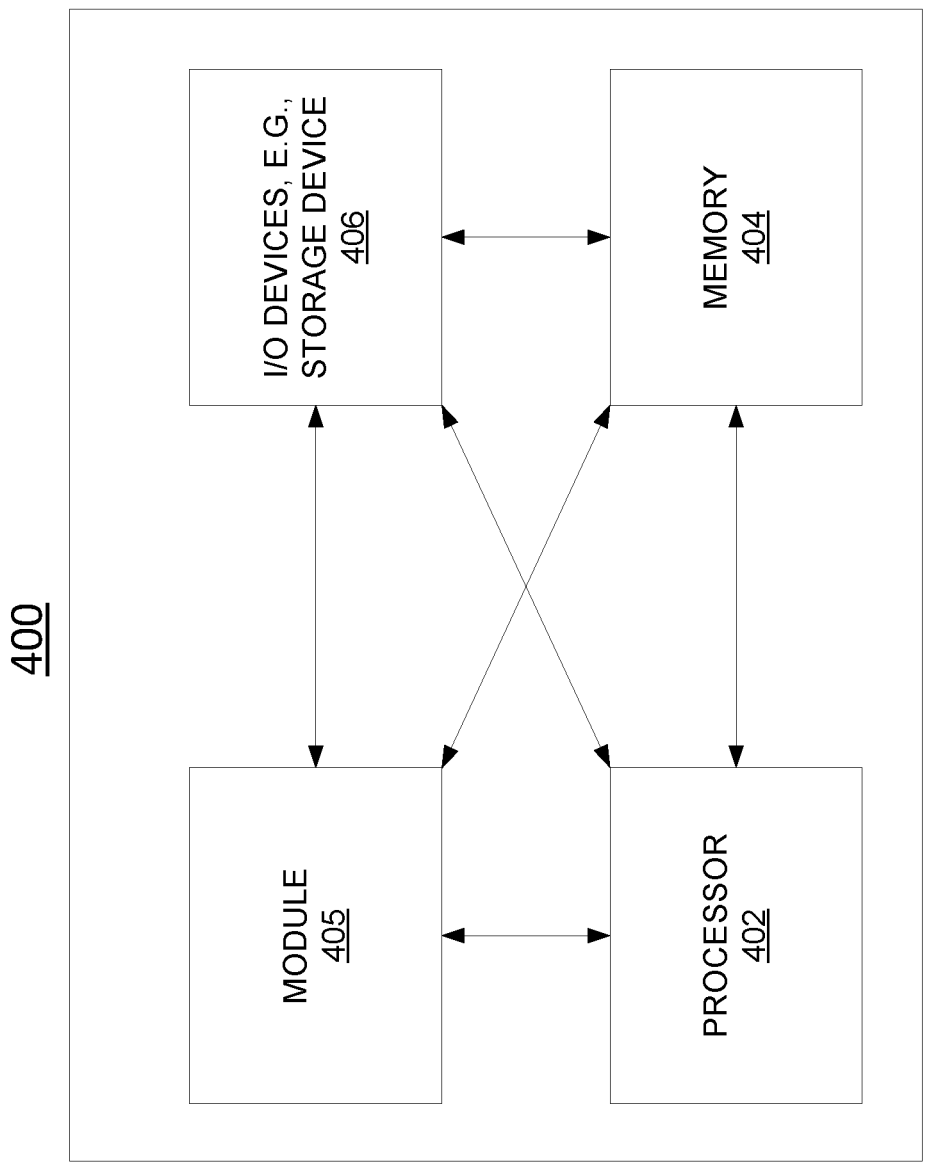
FIG. 4 illustrates an example high-level block diagram of a computing device specifically programmed to perform the steps, functions, blocks, and/or operations described herein.

In accordance with the present disclosure, each of the server(s) 104 may comprise a computing system or server, such as computing system 400 depicted in FIG. 4, and may individually or collectively be configured to provide one or more operations or functions for detecting via at least one detection model at least one health anomaly related to a physical condition of a user from behavioral data of a virtual representation of the user that is extracted from a data feed of a region of a virtual environment, such as illustrated and described in connection with the example method 300 of FIG. 3. It should be noted that as used herein, the terms "configure," and "reconfigure" may refer to programming or loading a processing system with computer-readable/computer-executable instructions, code, and/or programs, e.g., in a distributed or non-distributed memory, which when executed by a processor, or processors, of the processing system within a same device or within distributed devices, may cause the processing system to perform various functions. Such terms may also encompass providing variables, data values, tables, objects, or other data structures or the like which may cause a processing system executing computer-readable instructions, code, and/or programs to function differently depending upon the values of the variables or other data structures that are provided. As referred to herein a "processing system" may comprise a computing device including one or more processors, or cores (e.g., as illustrated in FIG. 4 and discussed below) or multiple computing devices collectively configured to perform various steps, functions, and/or operations in accordance with the present disclosure.

Thus, although only a single server 104 is illustrated, it should be noted that any number of servers may be deployed, and which may operate in a distributed and/or coordinated manner as a processing system to perform operations for detecting via at least one detection model at least one health anomaly related to a physical condition of a user from behavioral data of a virtual representation of user that is extracted from a data feed of a region of a virtual environment, in accordance with the present disclosure. In one example, server(s) may comprise a VR content server, or "virtual environment server," as described herein. In one example, database(s) (DB(s)) 106 may comprise one or more physical storage devices (e.g., a database server, or servers), to store various types of information in support of systems for detecting via at least one detection model at least one health anomaly related to a physical condition of a user from behavioral data of a virtual representation of user that is extracted from a data feed of a region of a virtual environment, in accordance with the present disclosure. For example, DB(s) 106 may store object detection and/or recognition models, event detection and/or recognition models, detection/classification models for classifying whether events are related to physical conditions of users, user data (including user device data), behavioral data of virtual user representations in a virtual environment, other user health data, and so forth that may be processed by server(s) 104 in connection with examples of the present disclosure for detecting via at least one detection model at least one health anomaly related to a physical condition of a user from behavioral data of a virtual representation of user that is extracted from a data feed of a region of a virtual environment. In addition, DB(s) 106 may also store data characterizing a virtual environment, and which may be used for rendering the virtual environment via user endpoint/access devices (e.g., devices 131-133, or the like). For instance, DB(s) 106 may store data characterizing the terrain of a virtual environment, buildings or other structures in the virtual environment, items or objects in the virtual environment, the virtual user representations that may be present in the virtual environment, rules describing how items or objects in the virtual environment may move, how virtual user representations may move through and interact with objects or other virtual user representations in the virtual environment, and so forth. For ease of illustration, various additional elements of network 102 are omitted from FIG. 1.

In one example, the access network(s) 122 may be in communication with one or more devices, such as devices 131 and 132. Similarly, access network(s) 120 may be in communication with one or more devices or systems, e.g., device 133, server(s) 124, DB(s) 126, etc. Access networks 120 and 122 may transmit and receive communications between devices 131-133, and server(s) 124 and/or DB(s) 126, server(s) 104 and/or DB(s) 106, other components of network 102, devices reachable via the Internet in general, and so forth.

In one example, each of the devices 131-133 may comprise any single device or combination of devices that may comprise a user endpoint device. For example, the devices 131-133 may each comprise a wearable computing device (e.g., smart glasses, an AR and/or VR headset or goggles, or the like), a laptop, a tablet computer, etc. In one example, each of the devices 131-133 may include one or more radio frequency (RF) transceivers for cellular communications and/or for non-cellular wireless communications. In addition, in one example, devices 131-133 may each comprise programs, logic or instructions to perform operations in connection with examples of the present disclosure for detecting via at least one detection model at least one health anomaly related to a physical condition of a user from behavioral data of a virtual representation of user that is extracted from a data feed of a region of a virtual environment. For example, devices 131-133 may each comprise a computing system or device, such as computing system 400 depicted in FIG. 4.

Access networks 120 and 122 may transmit and receive communications between such devices/systems, and server(s) 104, other components of network 102, devices reachable via the Internet in general, and so forth. In one example, the access networks 120 and 122 may comprise Digital Subscriber Line (DSL) networks, public switched telephone network (PSTN) access networks, broadband cable access networks, Local Area Networks (LANs), wireless access networks (e.g., an IEEE 802.11/Wi-Fi network and the like), cellular access networks, 3rd party networks, and the like. For example, the operator of network 102 may provide a cable television service, an IPTV service, or any other types of telecommunication service to subscribers via access networks 120 and 122. In one example, the access networks 120 and 122 may comprise different types of access networks, may comprise the same type of access network, or some access networks may be the same type of access network and others may be different types of access networks. In one example, the network 102 may be operated by a telecommunication network service provider. The network 102 and the access networks 120 and 122 may be operated by different service providers, the same service provider or a combination thereof, or may be operated by entities having core businesses that are not related to telecommunications services, e.g., corporate, governmental or educational institution LANs, and the like. In one example, each of access networks 120 and 122 may include at least one access point, such as a cellular base station, non-cellular wireless access point, a digital subscriber line access multiplexer (DSLAM), a cross-connect box, a serving area interface (SAI), a video-ready access device (VRAD), or the like, for communication with devices 131-133 and others.

In an illustrative example, users 1-3 may be engaged within a virtual environment, e.g., hosted by server(s) 104. In other words, users 1-3 may be "immersed" in the virtual environment. Accordingly, in one example, server(s) 104 may provide respective data feeds to devices 131-133 for devices 131-133 to generate different renderings of the virtual environment for users 1-3, respectively. For instance, device 131 may render the virtual environment from perspective 1 (151), device 132 may render the virtual environment from perspective 2 (152), and device 133 may render the virtual environment from perspective 3 (153). Each of the users 1-3 may have a different location and vantage/view within the virtual environment. In addition, each user may appear to others as a virtual user representation (e.g., an avatar such as an anthropomorphized animal or object, a cartoonified representation of the user, such as bitmoji or the like, a different character selected by the user, and so forth, or an accurate three dimensional rendering/model of the user generated by a computing device) within the virtual environment. In other words, the virtual representation is not an actual representation of the user such as an actual video feed of the user or an actual photograph of the user. Instead, the virtual representation is a computer generated image or graphics that is representative of the user. Thus, for instance, user 1 may see a representation of user 3 on the left and a representation of user 2 off in the distance. Similarly, user 3 may see a representation of user 1 on the right and a representation of user 2 in the distance. For instance, users 1 and 3 may be walking side by side in the direction of user 2. On the other hand, user 2 may see representations of users 1 and 3 in the distance. For instance, user 2 may be walking towards users 1 and 3 to meet up with them. In the present example, the virtual environment may be experienced by users 1-3 from a first-person perspective. However, it should be noted that in other examples, the virtual environment may be experienced in a different manner, such as from a perspective above and/or behind a virtual user representation of a respective user 1-3 (e.g., a "bird's eye view"). For illustrative purposes, an object 1 is also shown in FIG. 1, e.g., a virtual object that may be moved and interacted with by the virtual representations of users 1-3 within the virtual environment (and which, in one example, may be simulated in the physical world by force feedback gloves 141-143, e.g., via instructions from server(s) 104). For instance, each pair of force feedback gloves 141-143 may include a gyroscope, a compass, one or more accelerometers, and so forth. Force feedback gloves 141-143 may also include a plurality of actuators which may be controllable to provide positive force and/or movement of various portions of the hands of the respective users 1-3 (e.g., electromechanical actuators or motors, electro-hydraulic actuators, electro-pneumatic actuators, etc.). In one example, force feedback gloves 141-143 may also include transceivers for wireless communications, wired communication, etc.

In accordance with the present disclosure, server(s) 104 may include a health monitoring module (HMM) 107. For instance, a first one or more of server(s) 104 may host the virtual environment, while a second one or more of server(s) 104 may host the HMM 107. In other words, the HMM 107 may be a separate and distinct platform from the virtual environment server(s). In another example, the HMM 107 may comprise a separate process (or processes) on a shared hardware platform with the virtual environment host (e.g., the same one or more of server(s) 104). In one example, an HMM 107 may be user-specific. In other words, there may be multiple HMMs hosted by server(s) 104, e.g., one for each user, or one for each user that opts-in to health monitoring and alerting in accordance with the present disclosure.

For illustrative purposes, the HMM 107 may be associated with user 1. Accordingly, in one example, HMM 107 may obtain a data feed pertaining to a region of the virtual environment experienced by user 1 (e.g., the region of the virtual environment in which the virtual representation of user 1 is present). It should be noted that the virtual environment may represent a substantial volume of virtual space. As such, for each of the users 1-3 (and others), the server(s) 104 hosting the virtual environment may provide respective data feeds to devices 131-133 for rendering the virtual environment from perspectives 1-3, respectively. In other words, each data feed may include less than all of the data representing the state of the virtual environment at a given point in time, or times. For example, each of devices 1-3 may be provided with just enough data to render a respective one of the perspectives 1-3. Any visual or other data beyond the perspective may be omitted from the respective data feed. However, it should be noted that in one example, data for rendering aspects of the virtual environment that are just beyond the view/perspective may be included in the data feed. For instance, if user 1 (e.g., the virtual representation of user 1) is moving very quickly in the virtual environment or changes the direction of view very quickly, the data feed may include additional data to enable the device 131 to render from the changed perspective. Thus, some data of the feed may go unused for rendering, but may be available if needed depending upon the actions of user 1.

Similarly, the HMM 107 may obtain a data feed for the region of the virtual environment (e.g., representing less than all of the virtual environment). In one example, the data feed may be selected for HMM 107 by the server(s) 104 hosting the virtual environment as if the HMM 107 were another user in the system. For instance, in one example, a view/perspective of HMM 107 may be assumed to be a certain distance in front of and facing the virtual representation of user 1. In another example, the view/perspective of HMM 107 may be assumed to be facing the virtual representation of user 1, but in front of and above the virtual representation of user 1 within a space of the virtual environment (e.g., a "bird's-eye view" facing the virtual representation of user 1).

In one example, a data feed may comprise a volumetric video, a 360 degree video, or the like. In one example, a data feed may comprise visual data for a respective viewport (e.g., for device 131, a view from a current location (or one or more predicted locations)) within the virtual environment and in the current direction (or one or more predicted directions of view; for the HMM 107, a view toward the virtual representation of user 1, and at least including the virtual representation of user 1). In one example, the data feed for user 1 may be generated by server(s) 104 by blending data regarding fixed or relatively fixed features of the virtual environment (e.g., terrain, buildings, etc.), with data regarding moveable objects (e.g., object 1) and virtual user representations (e.g., virtual representations of user 2 and 3). Alternatively, or in addition, data regarding fixed or relatively fixed features of the virtual environment may initially be provided to device 131 and to HMM 107. Dynamic features may then be described to device 131 and to HMM 107 via subsequent data of the respective data feeds (e.g., changes in the perspective 1 of user 1, changes in the location of the virtual representation of user 1, and hence corresponding changes in the view/perspective of HMM 107, etc.). In any case, HMM 107 may thus obtain a data feed that provides a view of the virtual representation of user 1 within the virtual environment.

In accordance with the present disclosure, HMM 107 may then extract behavioral data of the virtual representation of user 1 from the data feed. In one example, the behavioral data may be extracted via one or more detection models (e.g., one or more machine learning models (MLMs)). For instance, the extracting of behavioral data may include detecting an event (e.g., a scenario, action, occurrence, or the like) of a defined event type via at least one detection model, and then gathering additional behavioral data relating to the event. For example, HMM 107 may detect, via applying the data feed to a detection model for "catching," that a virtual representation of user 1 is catching a virtual object (object 1). For instance, user 1 may be using force feedback gloves 141 so as to "catch" object 1. In response, HMM 107 may then extract data from the data feed for before and after the detection regarding movements of the virtual representation of user 1 within the data feed (e.g., whether the catch is successful or not, the speed of the movement of the virtual representation of user 1 towards the object, etc.). Notably, HMM 107 may not have access to the actual sensor feedback and control data for force feedback gloves 141. However, HMM 107 may extract movement data relating to the "catching" action from the visual data (e.g., the virtual object and/or the pertinent user(s)) of the data feed.

Similarly, HMM 107 may detect, via applying the data feed to a detection model for "throwing," that the virtual representation of user 1 is engaged or has engaged in an act of throwing (e.g., "throwing" object 1 (e.g., a virtual object) via use of the force feedback gloves 141). In response, HMM 107 may then extract more specific data relating to this event, such as whether the throw is accurate or not (e.g., whether the throw is close to an apparent intended target, the calculated speed of the throw, the observed range of motion of one or more limbs and/or other body parts of the virtual representation of user 1, etc.). In one example, HMM 107 may detect an acute health event via at least one detection model, such as the virtual representation of user 1 being wounded, the virtual representation of user 1 appearing to slip and fall, and so forth.

Figure 2:
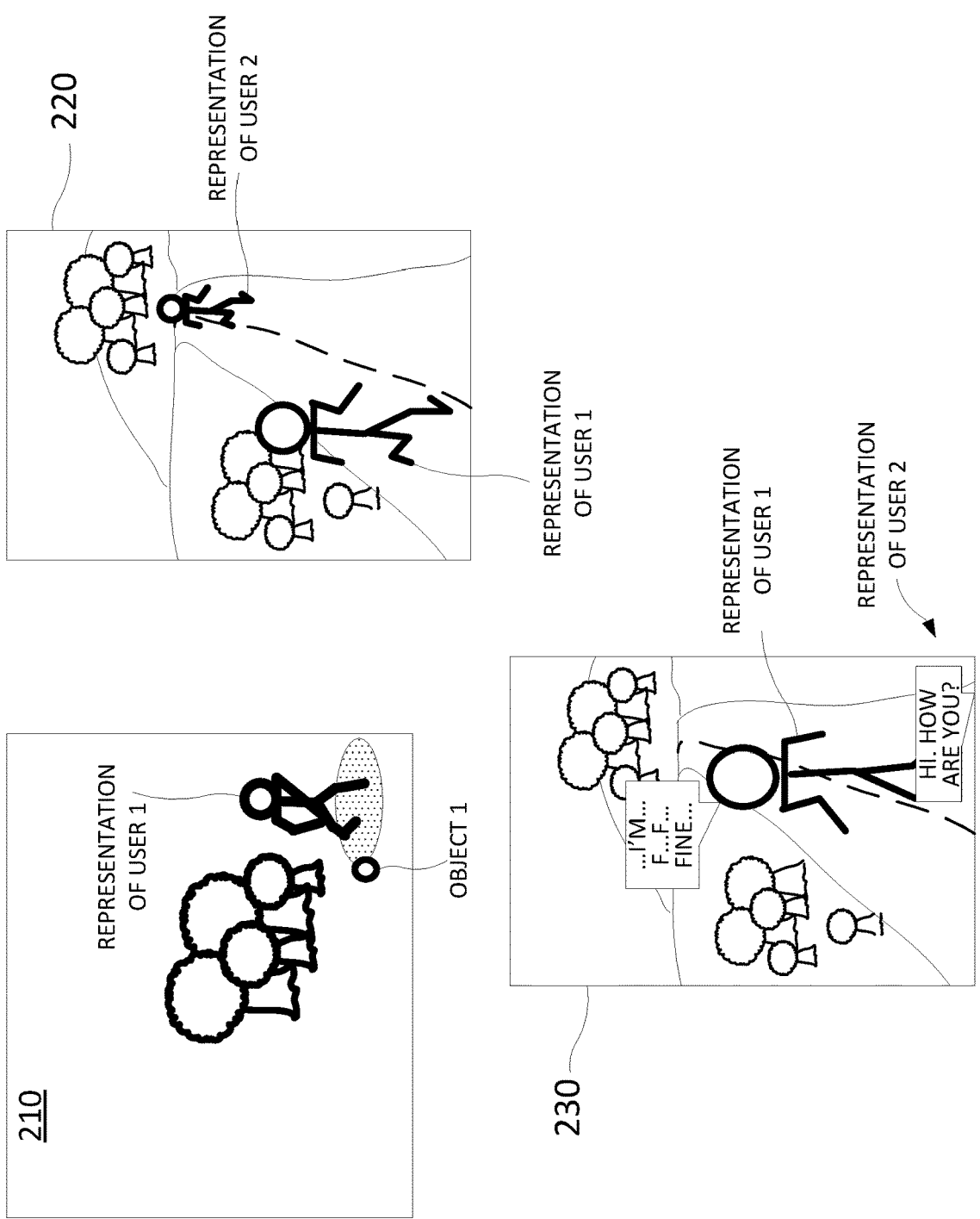
FIG. 2 illustrates examples of visual aspects of a user data feed of a virtual environment that may be scanned by a health monitoring module, in accordance with the present disclosure.

For instance, HMM 107 may detect that the virtual representation of user 1 is affected by a "gun wound" via applying the data feed to a detection model for "gun wound." In response, HMM may then extract additional data from the data feed, e.g., from before, during, and/or after the detection of the "gun wound" event, such as whether virtual representations of one or more other users are present, actions taken by such other virtual representation(s) indicated in the data feed, whether the virtual representation of user 1 engages in "normal" movements within a short duration of time after the detection of the "gun wound" event, and so forth. Similarly, HMM 107 may detect that the virtual representation of user 1 is affected by a "slip-and-fall" event via applying the data feed to a detection model for "slip-and-fall." In response, HMM may then extract additional data from the data feed, e.g., from before, during, and/or after the detection of the "slip-and-fall" event, such as whether the virtual representation of user 1 engages in "normal" movements within a short duration of time after the detection of the "slip-and-fall" event, whether one or more virtual objects is/are present (such as object 1, which may have caused the virtual representation of user 1 to slip-and-fall in a purely virtual manner by "stepping" on object 1, for instance), and so forth. In this regard, FIG. 2 illustrates examples of visual aspects of data feed(s) of a virtual environment that may be scanned by a health monitoring module. For instance, the examples of FIG. 2 may relate to user 1 and events that may be detected by HMM 107 of FIG. 1. In a first example 210, the HMM 107 may detect a slip-and-fall event of the virtual representation of user 1. In addition, the HMM 107 may detect object 1, which may be a potential cause of a "virtual" slip-and-fall.

To illustrate, server(s) 104 may generate (e.g., train) and store detection models that may be applied by HMM 107 (and/or other HMMs), in order to detect events of interest in user data feeds relating to the virtual environment. For instance, in accordance with the present disclosure, the detection models may be specifically designed for detecting types of events (e.g., actions, occurrences, or other scenarios). The types of events may include, for example, walking, running, cycling, swimming, flying, catching, throwing, shooting, etc.). The types of events may also include "acute" health events, such as "wound," "slip-and-fall," "collision," or the like. The detection models, or signatures, may be specific to particular types of visual/image and/or audio data in the data feed. For instance, with respect to a detection model that uses visual input, the input data may include low-level invariant image data, such as colors (e.g., RGB (red-green-blue) or CYM (cyan-yellow-magenta) raw data (luminance values) from a CCD/photosensor array), shapes, color moments, color histograms, edge distribution histograms, etc. Visual features may also relate to movement in a video or other visual sequences (e.g., visual aspects of a data feed of a virtual environment) and may include changes within images and between images in a sequence (e.g., video frames or a sequence of still image shots), such as color histogram differences or a change in color distribution, edge change ratios, standard deviation of pixel intensities, contrast, average brightness, and the like. In accordance with the present disclosure, one or more detection models may also be trained and deployed to detect other characteristics in the data feed that may relate to an event, such as detecting particular items, objects, or other physical aspects of an environment (e.g., a ball, a bat, a car, a truck, a tree, a shovel, fire, ice, snow, etc.).

In accordance with the present disclosure, a detection model may comprise a machine learning model (MLM) that is trained based upon the plurality of features available to the system (e.g., a "feature space"). For instance, one or more positive examples for a feature may be applied to a machine learning algorithm (MLA) to generate the detection model, or "signature" (e.g., a MLM). In one example, the MLM may comprise the average features representing the positive examples for an event or an object in a feature space. Alternatively, or in addition, one or more negative examples may also be applied to the MLA to train the MLM. The machine learning algorithm or the machine learning model trained via the MLA may comprise, for example, a deep learning neural network, or deep neural network (DNN), a generative adversarial network (GAN), a support vector machine (SVM), e.g., a binary, non-binary, or multi-class classifier, a linear or non-linear classifier, and so forth. In one example, the MLA may incorporate an exponential smoothing algorithm (such as double exponential smoothing, triple exponential smoothing, e.g., Holt-Winters smoothing, and so forth), reinforcement learning (e.g., using positive and negative examples after deployment as a MLM), and so forth. It should be noted that various other types of MLAs and/or MLMs may be implemented in examples of the present disclosure, such as k-means clustering and/or k-nearest neighbor (KNN) predictive models, support vector machine (SVM)-based classifiers, e.g., a binary classifier and/or a linear binary classifier, a multi-class classifier, a kernel-based SVM, etc., a distance-based classifier, e.g., a Euclidean distance-based classifier, or the like, and so on. In one example, a trained detection model may be configured to process those features which are determined to be the most distinguishing features of the associated event or object, e.g., those features which are quantitatively the most different from what is considered statistically normal or average from other events or objects that may be detected via a same system, e.g., the top 20 features, the top 50 features, etc.

In one example, detection models (e.g., MLMs) may be trained and/or deployed by HMM 107 (and/or other HMMs) to process a data feed associated with user 131 (or another user for a different HMM) to identify patterns in the features of the data feed that match the detection model(s) for the respective event(s) and/or object(s). In one example, a match may be determined using any of the visual features mentioned above, e.g., and further depending upon the weights, coefficients, etc. of the particular type of MLM. For instance, a match may be determined when there is a threshold measure of similarity among the features of the visual data from the data feed of user 1 and an event signature and/or object signature. Similarly, in one example, HMM 107 may apply an object detection and/or edge detection algorithm to identify possible unique items in visual data of the data feed for user 1 (e.g., without particular knowledge of the type of item; for instance, the object/edge detection may identify an object in the shape of a shovel in the visual data, without understanding that the object/item is a shovel). In this case, visual features may also include the object/item shape, dimensions, and so forth. In such an example, object recognition may then proceed as described above (e.g., with respect to the "salient" portions of the visual data).

In one example, detection models may be trained with labeled training data. For instance, slip-and-fall events in the virtual environment data feeds that are known to not involve an actual user slip-and-fall in the physical world may be labeled as "virtual only" events. Similarly, slip-and-fall events in virtual environment data feeds that are known to involve an actual user slip-and-fall in the physical world may be labeled as "real" events related to the physical condition of a user. For instance, users may confirm such events after-the-fact via user feedback to server(s) 104. Alternatively, or in addition, test users wearing helmets, elbow pads, kneed pads, and/or other protective clothing may further wear user VR interaction devices, such as VR headsets, force feedback gloves, etc. and may engage in slip-and-fall movements, for which corresponding actions of virtual user representations (e.g., avatars) may then be recorded in virtual environment data feeds. In this regard, it should be noted that various event detection models may be specific to different types of virtual user representations (e.g., one detection model for detecting slip-and-fall events relating to user representations of a type "skateboard," a different detection model for detecting slip-and-fall events relating to virtual user representations of a type "banana peel," and so forth). In addition, various event detection models may be specific to a virtual environment. For instance, the time to recover from a serious virtual "wound" in a first virtual environment may be longer or shorter than the time to recover in a second virtual environment. Similarly, detection/classification models such as those relating to "typical" movements of a virtual representation of a user, the accuracy of the virtual user representation in certain movements/actions, and so forth may be user specific, may be virtual user representation specific (e.g., where the user may change between user representations (e.g., the user has two or more avatars)), and/or may be virtual environment specific (e.g., there may be different virtual environments having different physics (e.g., a muddy surface, a sandy surface, a paved road surface, etc.), different virtual user representation capabilities (e.g., some virtual environments may provide for flying humans, while others do not)), and so forth.

In accordance with the present disclosure, the behavioral data may include movement/mobility data, e.g., gait data, posture data, or the like, facial expression data, speech data, reaction data (e.g., describing speed and timing), accuracy data (e.g., throwing or catching objects, hitting a target, etc.), and so forth. To illustrate, movement data may be derived in one of several ways. In a first example, the movement data may be extracted from the data feed by selecting data from the data feed that is specific to movement of parts of the virtual representation of user 1. For instance, the virtual representation of user 1 may be described in the data feed as a point cloud, and where points in the point cloud may move from frame to frame (e.g., time 1 to time 2, etc.). The points may be associated with joints, e.g., elbow joints, knee joints, torso, etc., such that the movement of points may characterize the movement of the virtual representation of user 1.

In one example, this movement data may be further processed to identify particular types of movement, e.g., applying this movement data to one or more detection models (e.g., one or more trained MLMs, such as described above) to detect that the virtual representation of user 1 is walking, running, sitting, swimming, flying (e.g., the virtual representation of the user 1 is in a virtual environment and hence it may be possible for the virtual representation of user 1 to be engaged in this action), etc. Thus, in some cases, behavioral data may be extracted and the type of event (e.g., action, motion, occurrence, or other scenario) may be determined from the behavioral data (e.g., via one or more detection models). However, in other cases, a type of event may be detected from the data feed (e.g., via one or more detection models) and the behavioral data that is more specific to the type of event may then be extracted.

In addition, in one example, detected type of motion information may be stored by HMM 107 (e.g., in a record in one of DB(s) 106), to track the long term mobility of the virtual representation of user 1 (and hence a level of physical movement of user 1 who controls the virtual representation of user 1). For instance, the virtual representation of user 1 may be recorded as walking 45 minutes, standing for 15 minutes, and sitting for 1 hour in the course of two hours immersed in the virtual environment. In this case, user 1 may be considered to be relatively active over the recorded duration. However, if the virtual representation of user 1 is recorded as sitting for the full two hours, user 1 may be considered to have been relatively sedentary during this time period. Thus, the recordation of the movement of the virtual representation of user 1 may be useful in identifying potential health events (e.g., too long without movement, insufficient movement within a designated time period, etc.).

Similarly, movement data related to particular types of movement may be recorded over time for a user and a "signature" may be trained/learned for the virtual representation of user 1. For instance, HMM 107 may train a model that learns the "typical" or "normal" walking characteristics of the virtual representation of user 1 in the virtual environment. Accordingly, the HMM 107 may also use such a model to detect when a current walking motion of the virtual representation of user 1 deviates from the "normal" walking pattern/signature for that user. For instance, the virtual representation of user 1 may appear to be limping in a current data feed, which may be detected by calculating a measure of deviation of the current walking pattern to the typical/normal walking pattern, or signature. Alternatively, or in addition, HMM 107 may train and/or deploy a detection model representing a typical walking pattern for a particular type of virtual user representation (e.g., a type of avatar of the virtual representation of user 1, where various other users may also have avatars of a same type from which the typical/normal walking pattern may be learned). In one example, the HMM 107 may record a time spent walking (e.g., distinguished from other actions via a first machine learning model (MLM)) and may further record a time and/or percentage of normal/typical walking versus abnormal/atypical walking (e.g., determined via a second MLM for determining typical versus atypical walking).

In accordance with the present disclosure, HMM 107 may further detect that at least one health anomaly that is exhibited in the behavioral data is related to a physical condition of user 1. To illustrate, the extracting of the behavioral data described above may include detecting an acute health event, such as a wound, a slip-and-fall, a collision, etc., affecting the virtual representation of user 1. Accordingly, HMM 107 may then further determine whether the "wound," "slip-and-fall," "collision," or the like is a virtual event related to the virtual representation of the user within the virtual environment or a "real" event that may physically affect user 1. For instance, the virtual representation of user 1 may be attacked in a gaming scenario and may lose a limb or may be bleeding, etc., but this may be part of the game mode/presentation. Thus, to detect that an acute health event is "real" and not "virtual," in one example HMM 107 may apply a further detection/classification model that has been trained to learn how long it takes for the virtual representation of user 1 to reset to a different condition after an apparent acute health event that is purely virtual, such as losing a limb, being shot, etc. in a virtual game.

For instance, referring again to the example 210 of FIG. 2, if the virtual representation of user 1 falls to the ground, but reverts to a standing position within 5-10 seconds, continues moving, etc., this may be a virtual event that may be detected/determined as such via the associated detection/classification model. On the other hand, if the virtual representation of user 1 remains prone, holding a limb, etc. for a more extended period of time, this can then be detected as a potential real-world event via the associated detection/classification model. Such a detection/classification model may thus utilize behavioral data such as visual data from before and after the detected event, gait, posture, and/or movement data extracted from the visual data, etc. as inputs. Alternatively, or in addition, such a detection model may be further trained in accordance with audio data. For instance, a virtual "wound" may be accompanied by one or several automatic sounds in the virtual environment that a trained model may learn to be "expected" in connection with such a virtual event. As such, other sounds of real distress by user 1 may not fall within this pattern and tend to cause the detection/classification model to determine that such an event is not "virtual" but is a potential real wound (e.g., a crying sound from user 1). Similarly, in one example, HMM 107 may initially detect an acute health event of "slip-and-fall" for example, and may then activate additional detection models to detect virtual objects that are present. As such, any detected virtual objects may comprise additional input(s) to a detection/classification model for determining whether the "slip-and-fall" is real or purely virtual. For instance, a detection of one or more virtual objects on the ground such as a ball or banana peel may tend to indicate that the event is purely virtual when input to the detection/classification model.

In another illustrative example, the behavioral data may not necessarily include a detected "acute" health event. For instance, the behavioral data may include data relating to the times the virtual representation of user 1 is "active" vs. "inactive," when the virtual representation of user 1 is walking, running, sitting, standing, etc. Similarly, the behavioral data may include timing data, movement data, etc. for multiple instances of different actions of the virtual representation of user 1. For instance, a first detection model may be trained to detect a spin-jump move, or sequence of movements within the virtual environment. In addition, user 1 may be generally skilled at executing spin-jump sequences which may be learned by a second detection/classification model. If the virtual representation of user 1 deviates from a high skill-level movement, this may be detected as being a potential health event related to a physical condition of the user. For instance, if the virtual representation of user 1 is to jump a gap in the virtual environment with a spin-jump sequence and fails several times, whereas the user typically has no issues with landing such a movement, this may be caused by the user being fatigued, sick, or having another ailment.

Similarly, a user may be an accurate shooter which may be learned by a trained detection/classification model for detecting whether the user's shooting is "normal" (e.g., accurate) or abnormal (e.g., inaccurate), or which may be scored by a level of inaccuracy, (e.g., how far from accurate is the user's current shooting?). In one example, a health anomaly relating to a physical condition of user 1 may be determined when the accuracy of user 1's movement may diminish by a certain threshold percentage, e.g., over the course of a defined period (e.g., 50% accuracy within a 30 minute sliding window when the user has a long-term average accuracy of 85% may be a cause for alerting a health anomaly relating to a physical condition of user 1 (which may be detected and alerted via the detection/classification model output, or which may be compiled from the detection/classification model output(s) over a sliding time window, for example)). In one example, an additional detection model may be applied to identify a target or likely target of user 1. For instance, the target may be identified as a most salient object in the visual data in accordance with an image salience detection algorithm (which may further include an object/edge detection algorithm to distinguish an object from other objects, etc.). In one example, HMM 107 may query a server hosting the virtual environment and/or the user device 131 as to a difficulty level or setting for user 1. For instance, user 1 may select an "enhanced difficulty" mode of a game, which may cause the accuracy of user 1 to decline significantly from an average or normal accuracy, cause the user to execute spin-jump sequences less precisely (e.g., presenting a more challenging terrain, presenting a storming environment (e.g., raining, sleeting, or snowing), etc.), and so forth. Thus, for example, a decline in accuracy may not be considered as a health event relating to a physical condition of the user if a difficulty level has been increased. Instead, HMM 107 may train a new model and/or retrain an existing model to learn a new baseline/average accuracy at this new difficulty level.

It should be noted that certain movements may be executed via one or more VR interactive components, such as force feedback gloves 141, a treadmill, footpads, or the like. However, in another example, movements of the virtual representation of user 1 may not have a direct relationship with movements of user 1 in a physical environment. For instance, the virtual representation of user 1 may be caused to execute spin-jump movements via one or more inputs of user 1 via a control pad, a keyboard, or the like. Alternatively, or in addition, gestures via force feedback gloves 141 may be received by one of the servers 104 hosting the virtual environment, which may be interpreted as a spin-jump movement (e.g., as opposed to movements of hands, arms, and or other limbs corresponding to the movements of force feedback gloves 141.

Similarly, FIG. 2, illustrates a second example 220 in which the virtual representation of user 1 may be observed to be jogging with the virtual representation of user 2. In one example, the HMM 107 may detect that user 1 is "jogging," e.g., via applying the data feed of the virtual environment associated with user 1 to a detection model for "jogging," a multi-class detection model (e.g., where the output is "jogging"), etc. In addition, HMM 107 may then further determine that the virtual representation of user 1 is slower than an average running pace for user 1. For instance, the virtual representation of user 1 may often engage in virtual jogging with the virtual representation of user 2. In addition, the representation of user 1 may typically be faster than the virtual representation of user 2 (and faster than a currently observed pace of jogging movement). For example, the distance covered per second, per minute, etc., within the virtual environment may be significantly less than the average jogging pace of the virtual representation of user 1, e.g., 20 percent slower than a long term average pace, 40 percent slower than the long term average pace, etc. Thus, in such case, HMM 107 may also detect a health anomaly that is related to a physical condition of user 1, and which does not appear to have a purely virtual cause. It should be noted that in one example the user 1 may actually engage a treadmill for the jogging, and the server(s) 104 hosting the virtual environment may move the virtual representation of user 1 through the virtual environment in accordance with speed and/or direction data from the treadmill. However, the HMM 107 does not necessarily have access to the raw data from such treadmill, but only receives a data feed from the server(s) 104 hosting the virtual environment. Thus, HMM 107 is tasked with recognizing the type of event (e.g., "jogging"), determining a pace, and comparing the pace to an average pace and/or jogging "signature"/classification model associated with the virtual representation of user 1 (which may have a non-human form), all from the virtual environment data feed that may be provided to/obtained by the HMM 107.

As noted above, a health event related to a physical condition of a user may alternatively or additionally be determined from audio data from a data feed of the virtual environment. To illustrate, FIG. 2 includes a third example 230 in which a virtual representation of user 1 may be verbally interacting with a virtual representation of user 2 in the virtual environment. In this case, HMM 107 may apply the audio data from the data feed to a detection/classification model that may be trained to distinguish between "normal" and "abnormal" speech of the virtual representation of user 1. It should be noted that the voice of the virtual representation of user 1 may not be a true voice of user 1, but may be transformed in some manner and added to the data feed of the virtual environment. For instance, the true voice/speech of user 1 may be captured via device 131, uploaded to server(s) 104, and transformed via one or more filters, e.g., to make the voice sound like an anthropomorphized animal or inanimate object, to make the voice sound like a famous character, and so forth. Continuing with the third example 230 of FIG. 2, the virtual representation of user 1 may be observed to be stuttering or slurring. This condition may be detected, for example, via a detection model trained to use audio features as inputs and to detect stuttering and/or slurring of virtual user representations of a particular type (e.g., user avatars of a "dog" type may have specific detection model(s) for these types of speech incidents, while virtual user representations of a "cat" type may have one or more other detection models). Alternatively, or in addition, virtual user representation-specific detection models for "normal" vs. "abnormal" speech, or "slurring" vs. "abnormal" speech may be applied.

In one example, HMM 107 may generate an alert in response to the detecting of the at least one health anomaly, and more specifically in response to determining that the at least one health anomaly is related to the physical condition of the user (e.g., and is not a purely virtual event). For instance, the alert can be sent from HMM 107 to the device 131 of user 1. The alert can include a detected/suspected health event related to the physical condition of user 1, such as "slip-and-fall." In one example, the alert may include a query to the user, such as "are you ok?" for a slip-and-fall event that appears to be real and not virtual (e.g., the virtual representation of user 1 is detected standing up slowly, or does not get up at all, as determined by HMM via a detection model that expects user to recover quickly for a virtual slip-and-fall (and/or for a physical/real-world slip-and-fall that did not result in injury)). The alert and/or query may be presented as an audio alert via device 131, may be presented visually such as a text box appearing within the first perspective of the virtual environment that is presented to user 1 via device 131, and so forth. User 1 may similarly respond via voice response, gesture (such as clicking a virtual button using force feedback gloves 141), text input via a keyboard, and so forth. In one example, an alert may alternatively or additionally be transmitted by HMM 107 to a medical entity designated by the user or that is assigned to a location associated with the user, a caregiver designated by the user, and so forth.

In addition, although the foregoing example(s) is/are described and illustrated in connection with a single virtual environment, it should again be noted that in one example, users may be tracked across several virtual environments, e.g., by the same or a different HMM 107. In one example, HMM 107 may adjust the use of various detection models accordingly (e.g., to use the virtual environment-specific detection models that are tuned to the type of virtual representation and the characteristics of the virtual environment (e.g., the physics thereof or the severity of certain virtual events/action; for example, being virtually hit in one virtual environment may cause the virtual representation of a user to be deactivated/immobilized for 30 seconds, whereas in another virtual environment, the virtual representation of the user may be removed from the virtual environment and may re-enter five minutes later)).

In one example, the HMM 107 may be provided with data feeds representing several views of the virtual representation of user 1, such as akin to a computed tomography (CT) scan or obtaining a set of magnetic resonance imaging (MRI) images. For instance, the HMM 107 may apply detection models to visual data from several perspectives, any of which may result in the detection of a health condition/event. In another example, HMM 107 may apply one or more detection models to contemporaneous visual data from several perspectives (e.g., multiple inputs to each of the one or more detection models). It should also be noted that the example of FIG. 1 illustrates just one example of user devices that may be used to interact with/experience a virtual environment. As such, it should be noted that in other, further, and different examples, users may alternatively or additionally interact with and experience a virtual environment using fans, heating and/or cooling elements, e.g., climate control systems, network-connected cycles, shoes, and or treadmills, a network of body worn sensors to more precisely detect movements of limbs, and so forth.

It should also be noted that the system 100 has been simplified. In other words, the system 100 may be implemented in a different form than that illustrated in FIG. 1. For example, the system 100 may be expanded to include additional networks and additional network elements (not shown) such as wireless transceivers and/or base stations, border elements, routers, switches, policy servers, security devices, gateways, a network operations center (NOC), a content distribution network (CDN) and the like, without altering the scope of the present disclosure. In addition, system 100 may be altered to omit various elements, substitute elements for devices that perform the same or similar functions and/or combine elements that are illustrated as separate devices.

As just one example, one or more operations described above with respect to server(s) 104 and/or HMM 107 may alternatively or additionally be performed by server(s) 124, and vice versa. In this regard, DB(s) 126 may store the same or similar information as DB(s) 106 as described above. Similarly, although the foregoing is described in connection with HMM 107 being part of server(s) 104, in another example, HMM 107 may instead be installed as a standalone module within one of the devices 111-113, as a third-party service, or the like.

In addition, although a single server 104 and single server 124 are illustrated in the example of FIG. 1, in other, further, and different examples, the same or similar functions may be distributed among multiple other devices and/or systems within the network 102, access network(s) 120 or 122, and/or the system 100 in general that may collectively provide various services in connection with examples of the present disclosure for detecting via at least one detection model at least one health anomaly related to a physical condition of a user from behavioral data of a virtual representation of the user that is extracted from a data feed of a region of a virtual environment. Additionally, devices that are illustrated and/or described as using one form of communication (such as a cellular or non-cellular wireless communications, wired communications, etc.) may alternatively or additionally utilize one or more other forms of communication. Thus, these and other modifications are all contemplated within the scope of the present disclosure.

FIG. 3 illustrates a flowchart of an example method 300 for detecting via at least one detection model at least one health anomaly related to a physical condition of a user from behavioral data of a virtual representation of the user that is extracted from a data feed of a region of a virtual environment. In one example, steps, functions and/or operations of the method 300 may be performed by a device or apparatus as illustrated in FIG. 1, e.g., by server(s) 104 and/or servers(s) 124, such as a health monitoring module (HMM), or any one or more components thereof, or by server(s) 104 and/or servers(s) 124, and/or any one or more components thereof in conjunction with one or more other components of the system 100, such as devices 131-133, and so forth. In one example, steps, functions and/or operations of the method 300 may be performed by a user device as illustrated in FIG. 1, e.g., such as by one of the devices 131-133, or any one or more components thereof, or by devices 131-133, and/or any one or more components thereof in conjunction with one or more other components of the system 100, and so forth. In one example, the steps, functions, or operations of method 300 may be performed by a computing device or processing system, such as computing system 400 and/or hardware processor element 402 as described in connection with FIG. 4 below. For instance, the computing system 400 may represent any one or more components of the system 100 that is/are configured to perform the steps, functions and/or operations of the method 300. Similarly, in one example, the steps, functions, or operations of the method 300 may be performed by a processing system comprising one or more computing devices collectively configured to perform various steps, functions, and/or operations of the method 300. For instance, multiple instances of the computing system 400 may collectively function as a processing system. For illustrative purposes, the method 300 is described in greater detail below in connection with an example performed by a processing system. The method 300 begins in step 305 and proceeds to step 310.

At step 310, the processing system obtains a data feed of a region of a virtual environment associated with a virtual representation of a user within the virtual environment. For instance, the processing system may comprise a health monitoring module (HMM) as described herein. In one example, the processing system may be a processing system of an endpoint device of the user that is used to access the virtual environment. In such case, the data feed may be obtained from a server, or servers, hosting the virtual environment, for example. In another example, the processing system may comprise a processing system of a server hosting the virtual environment and the method 300 may be performed via at least one first process that is distinct from at least one second process that is for hosting the virtual environment. In such case, the at least one second process may provide the data feed of the region of the virtual environment. In still another example, the processing system may be a processing system of a first server and the virtual environment may be hosted via at least a second server, where the at least the second server provides the data feed of the region of the virtual environment.

The virtual representation of the user may comprise an avatar, for example, such as an anthropomorphized animal or object, a cartoonified representation of the user, such as bitmoji or the like, a different character selected by the user, and so forth. It should be noted that the server(s) hosting the virtual environment may provide the structure of the virtual environment via the data feed (e.g., permanent or semi-permanent features such as ground/terrain, buildings, trees, etc.), as well as transitional features of the virtual environment (e.g., virtual representations of users, their movements, sounds, interactions with each other, etc., other moveable items/objects that are purely virtual or are virtual representations of real world objects that are interacted with by one or more users and simulated via the interactions of the virtual representation(s) of the user(s) with one or more virtual objects representing the real-world object(s), and so forth). In one example, the second server may receive respective upload feeds from one or more user endpoint devices (e.g., describing the movements and actions, speech, and other user inputs) and may merge the received upload feeds or aspects of the received upload feeds to represent a current state of the virtual environment. From the state of the virtual environment, the server(s) may then generate user-specific data feeds for the respective user devices to render the experience of the virtual environment for a respective user. Thus, for example, the data feed may be selected to include visual and audio data from a region of the virtual environment in which a user (e.g., the virtual representation of the user) is currently located. In one example, the visual data may comprise visual data from a perspective, field-of-view, or "viewport" of the user (and may exclude visual data that is not within the field-of-view, or not anticipated to be within the field-of-view according to a prediction algorithm).

However, as noted above, a health monitoring module (HMM) may receive a data feed that includes visual data from one or more perspectives viewing the virtual representation of the user, e.g., a face-on view, a birds-eye view, etc. Thus, the data feed obtained at step 310 may include visual data from one or more of such perspectives. It should be noted that the data feed may include multiple communications from the server(s) hosting the virtual environment. In one example, the data feed may provide initial data to render the fixed or relatively fixed features in the region of the virtual environment, while subsequent portions of the data feed may include additional data for rendering transitional features. It should also be noted that the term "data feed" may include visual and/or audio data received on an ongoing basis over a period of time, e.g., for continuous health monitoring.

At step 320, the processing system extracts behavioral data of the virtual representation of the user from the data feed. The behavioral data may include one or more of gait data, posture data, facial expression data, speech data, mobility data, reaction data (e.g., speed, timing, or acceleration), accuracy data (e.g., for throwing, shooting, jumping, etc.), and so forth. In one example, step 320 may comprise first detecting at least one type of event via at least one detection model (e.g., at least one "second" detection model) for detecting the at least one type of event. For instance, the at least one detection model may be a machine learning model that is trained to detect "running," "walking," "jumping," "swimming," "throwing," "catching," "sitting," "standing," etc. In one example, the at least one type of event may include an acute health event, e.g., a type of event defined by an associated detection model. For instance, an acute health event may be "loss of limb," "slip-and-fall," "hit in head," "shot by projectile," "wound," "bleeding," "colliding," and so forth. The at least one detection model may use visual and/or audio data from the data feed as described above.

In one example, step 320 may include detecting an event (e.g., an occurrence, action, scenario, etc.) via at least one detection model and then gathering additional behavioral data relating to the detected event. For example, the processing system may detect that the virtual representation of the user is catching a virtual object and may then gather behavioral data from before and after regarding the virtual representations' movement, whether the catch is successful or not, etc. In another example, the processing system may detect that the virtual representation of the user is shooting (or has shot a projectile) and may then extract additional data regarding whether the shot is accurate or not (e.g., whether the shot hit what appears to be the intended target). In another example, step 320 may include extracting gait data, posture data, facial expression data, speech data, mobility data, reaction data (e.g., speed, timing, acceleration, position, etc.), accuracy data (e.g., for throwing, shooting, running, etc.), and so forth and then further detecting a noticeable change in the gait, posture, and/or mobility data, detecting a potential stroke event via an analysis of the facial expression data (e.g., drooping facial features such as smiling only on one side of the face), detecting a falling asleep event (or dozing off event with drooping eye lids) while gaming via an analysis of the facial expression data, etc. In other words, the at least one detection model may take gait data, posture data, facial expression data, speech data, mobility data, reaction data (e.g., speed, timing, acceleration, position, etc.), accuracy data (e.g., for throwing, shooting, etc.), and so forth as input(s).

At step 330, the processing system detects at least one health anomaly related to a physical condition of the user from the behavioral data via at least one detection model (e.g., at least one "first" detection model) for detecting the at least one health anomaly. For instance, in one example, step 330 may include determining that an acute health event detected at step 320 is associated with the physical condition of the user. This may include determining that the acute health event is not a virtual event related to the virtual representation of the user within the virtual environment (e.g., a purely virtual event). For example, the virtual representation of the user may be attacked in a gaming scenario and may lose a limb or may be bleeding, etc. However, this may be part of the game and may not physically affect the user. In one example, the at least one (first) detection model may be trained and learned how long it takes for the virtual representation of user to reset to a different condition after an acute health event that is purely virtual. Thus, for example, behavioral data may be input to the at least one (first) detection model; the output may indicate a classification of whether the acute health event is "real" or "virtual." To illustrate, if the virtual representation of the user resets from a prone position to a standing position after a short period of time and the virtual representation of the user continues moving, the event may be a virtual event. However, if the virtual representation of the user remains prone, holding a limb, etc., this can then be flagged as a potential real-world event that is associated with the physical condition of the user.

In one example, the at least one (second) detection model that may be applied at step 320 may be a higher level model to detect a type of action in general. In addition, the extracting of step 320 may obtain more specific behavioral data that may be input to the at least one (first) detection model at step 330 to determine: (1) if the event is related to a physical condition of user or if the behavior and/or event/occurrence is virtual (e.g., virtual wound vs. real wound, virtual slip and fall vs. real slip and fall, virtual collision vs. real collision, etc.) and/or (2) if the behavioral data is anomalous for the virtual representation of the user (e.g., whether the virtual representation of the user catching or throwing poorly as compared to typical/average performance of the virtual representation of the user, whether the virtual representation of the user being inaccurate as compared to a typical accuracy, e.g., for throwing, shooting, etc.). The type of determination (1 or 2) may depend on the type of health event being detected, e.g., an acute health event versus a deteriorating performance of the user (which may relate to a physical condition, such as lack of sleep, poor nutrition, dehydration, lack of physical movement in the real world, etc.).

Accordingly, in one example, step 330 may include applying at least a portion of the behavioral data to the at least one detection model, obtaining an indication of the health anomaly as an output of the at least one detection model, and determining that the health anomaly is related to the physical condition of the user in response to the obtaining of the indication of the health anomaly as the output of the at least one detection model. In addition, the at least one (first) detection model may be trained from a training data set comprising at least a portion of the behavioral data that is extracted at step 320. For example, one or more detection/classification model(s) may be trained for reaction timing for different actions within the virtual environment. Likewise, detection/classification model(s) may be trained for execution of different movements within the virtual environment (e.g., a virtual user representation is generally skilled at executing spin jump sequences; if the virtual user representation deviates from this, it may be detected via the detection model). Similarly, a user may be an accurate shooter, but the user's accuracy may diminish by a threshold percentage, which may be detected and alerted via the detection model output.

In one example, verifying that the health anomaly is related to the physical condition of the user may further be performed via biometric data of the user. For instance, the biometric data of the user may comprise an additional input to the at least one (first) detection model (and the at least one (first) detection model may be so trained to utilize such biometric data as an additional input/predictor). For instance, a detected slip-and-fall accompanied by a blood-oxygen level below 90 percent (e.g., detected via an oximeter) may be a strong indicator that the user has passed out and fallen down in real life and that the slip-and-fall event is not a purely virtual event. The biometric data may be obtained from a wearable device/sensor that is in communication with the processing system directly and/or via one or more intermediate devices and/or networks.

At step 340, the processing system generates an alert in response to the detecting of the at least one health anomaly that is related to the physical condition of the user. For instance, the alert may be provided to one or more of: an endpoint device of the user that is used to access the virtual environment, a medical entity designated by the user or that is assigned to a location associated with the user, a caregiver designated by the user, and so forth. For instance, the caregiver can be a parent of a child or a child of an older adult user, a medical entity can be the user's doctor, or a doctor or hospital that is local to a current location of the user, and so forth. In one example, the alert may alternatively or additionally be sent to a user endpoint device of another user engaged in the virtual environment to inform the other user of a potential problem with the user.

In one example, the alert may include a query to the user, such as "are you ok?" for a slip-and-fall event or a collision event that appears to be real and not virtual. The alert and/or query may be presented as an audio alert, may be presented visually such as a text box appearing within the first perspective of the virtual environment that is presented to the user via a user endpoint device (e.g., a VR headset or the like), and so forth. Following step 340, the method 300 proceeds to step 395. At step 395, the method 300 ends.

It should be noted that the method 300 may be expanded to include additional steps, or may be modified to replace steps with different steps, to combine steps, to omit steps, to perform steps in a different order, and so forth. For instance, in one example, the processing system may repeat one or more steps of the method 300, such as performing steps 310-330 on an ongoing basis until a health event related to a physical condition of the use is detected, performing step 310-340 for other users, and so forth. In one example, the method 300 may include training one or more detection models (e.g., MLMs) for detecting various events. The detection models may be user specific (e.g., specific to the virtual representation of the user) and/or may be specific to the type of virtual user representation. Alternatively, or in addition, the detection models may be specific to the virtual environment (e.g., from among a plurality of virtual environments that are accessible to and that are accessed by the user). In this regard, the method 300 may further include gathering training data relevant to the event and that is specific to the virtual user/users representation, type of virtual user representation, and/or virtual environment. It should also be noted that the processing system may be for detecting health anomalies from different instances of behavioral data associated with at least one virtual representation of the user extracted from different data feeds of a plurality of different virtual environments. In other words, the tracking and alerting may be performed on a virtual environment by virtual environment basis, where the data feeds from different virtual environments may be obtained by the processing system depending upon which virtual environment the user is currently experiencing. In various other examples, the method 300 may further include or may be modified to comprise aspects of any of the above-described examples in connection with FIGS. 1 and 2, or as otherwise described in the present disclosure. Thus, these and other modifications are all contemplated within the scope of the present disclosure.

In addition, although not expressly specified above, one or more steps of the method 300 may include a storing, displaying and/or outputting step as required for a particular application. In other words, any data, records, fields, and/or intermediate results discussed in the method 300 can be stored, displayed and/or outputted to another device as required for a particular application. Furthermore, operations, steps, or blocks in FIG. 3 that recite a determining operation or involve a decision do not necessarily require that both branches of the determining operation be practiced. In other words, one of the branches of the determining operation can be deemed as an optional step. However, the use of the term "optional step" is intended to only reflect different variations of a particular illustrative embodiment and is not intended to indicate that steps not labelled as optional steps to be deemed to be essential steps. Furthermore, operations, steps or blocks of the above described method 300 can be combined, separated, and/or performed in a different order from that described above, without departing from the example embodiments of the present disclosure.

FIG. 4 depicts a high-level block diagram of a computing system 400 (e.g., a computing device or processing system) specifically programmed to perform the functions described herein. For example, any one or more components, devices, and/or systems illustrated in FIG. 1 or described in connection with FIG. 2 or 3, may be implemented as the computing system 400. As depicted in FIG. 4, the computing system 400 comprises a hardware processor element 402 (e.g., comprising one or more hardware processors, which may include one or more microprocessor(s), one or more central processing units (CPUs), and/or the like, where the hardware processor element 402 may also represent one example of a "processing system" as referred to herein), a memory 404, (e.g., random access memory (RAM), read only memory (ROM), a disk drive, an optical drive, a magnetic drive, and/or a Universal Serial Bus (USB) drive), a module 405 for detecting via at least one detection model at least one health anomaly related to a physical condition of a user from behavioral data of a virtual representation of the user that is extracted from a data feed of a region of a virtual environment, and various input/output devices 406, e.g., a camera, a video camera, storage devices, including but not limited to, a tape drive, a floppy drive, a hard disk drive or a compact disk drive, a receiver, a transmitter, a speaker, a display, a speech synthesizer, an output port, and a user input device (such as a keyboard, a keypad, a mouse, and the like).

Although only one hardware processor element 402 is shown, the computing system 400 may employ a plurality of hardware processor elements. Furthermore, although only one computing device is shown in FIG. 4, if the method(s) as discussed above is implemented in a distributed or parallel manner for a particular illustrative example, e.g., the steps of the above method(s) or the entire method(s) are implemented across multiple or parallel computing devices, then the computing system 400 of FIG. 4 may represent each of those multiple or parallel computing devices. Furthermore, one or more hardware processor elements (e.g., hardware processor element 402) can be utilized in supporting a virtualized or shared computing environment. The virtualized computing environment may support one or more virtual machines which may be configured to operate as computers, servers, or other computing devices. In such virtualized virtual machines, hardware components such as hardware processors and computer-readable storage devices may be virtualized or logically represented. The hardware processor element 402 can also be configured or programmed to cause other devices to perform one or more operations as discussed above. In other words, the hardware processor element 402 may serve the function of a central controller directing other devices to perform the one or more operations as discussed above.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a computing device, or any other hardware equivalents, e.g., computer-readable instructions pertaining to the method(s) discussed above can be used to configure one or more hardware processor elements to perform the steps, functions and/or operations of the above disclosed method(s). In one example, instructions and data for the present module 405 for detecting via at least one detection model at least one health anomaly related to a physical condition of a user from behavioral data of a virtual representation of the user that is extracted from a data feed of a region of a virtual environment (e.g., a software program comprising computer-executable instructions) can be loaded into memory 404 and executed by hardware processor element 402 to implement the steps, functions or operations as discussed above in connection with the example method(s). Furthermore, when a hardware processor element executes instructions to perform operations, this could include the hardware processor element performing the operations directly and/or facilitating, directing, or cooperating with one or more additional hardware devices or components (e.g., a co-processor and the like) to perform the operations.

The processor (e.g., hardware processor element 402) executing the computer-readable instructions relating to the above described method(s) can be perceived as a programmed processor or a specialized processor. As such, the present module 405 for detecting via at least one detection model at least one health anomaly related to a physical condition of a user from behavioral data of a virtual representation of the user that is extracted from a data feed of a region of a virtual environment (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium may comprise a physical device, a hardware device, or a device that is discernible by the touch. More specifically, the computer-readable storage device or medium may comprise any physical devices that provide the ability to store information such as instructions and/or data to be accessed by a processor or a computing device such as a computer or an application server.

While various examples have been described above, it should be understood that they have been presented by way of example only, and not limitation. Thus, the breadth and scope of a preferred example should not be limited by any of the above-described examples, but should be defined only in accordance with the following claims and their equivalents.

What is claimed is:

1. A method comprising:
   obtaining, by a processing system including at least one processor, a visual data feed of a region of a virtual environment associated with a virtual representation of a user within the virtual environment, wherein the virtual representation of the user comprises an avatar;
   extracting, by the processing system, behavioral data of the virtual representation of the user from the visual data feed;
   detecting, by the processing system, at least one health anomaly related to a physical condition of the user from the behavioral data via at least one first detection model for detecting the at least one health anomaly, wherein the at least one first detection model is trained from a training data set comprising at least a portion of the behavioral data that is extracted; and
   generating, by the processing system, an alert in response to the detecting of the at least one health anomaly that is related to the physical condition of the user.

2. The method of claim 1, wherein the processing system is a processing system of an endpoint device of the user that is used to access the virtual environment.

3. The method of claim 1, wherein the processing system comprises a processing system of a server hosting the virtual environment, wherein the method is performed via at least one first process that is distinct from at least one second process that is for hosting the virtual environment.

4. The method of claim 3, wherein the at least one second process provides the visual data feed of the region of the virtual environment.

5. The method of claim 1, wherein the processing system is a processing system of a first server, and wherein the virtual environment is hosted via at least a second server, wherein the at least the second server provides the visual data feed of the region of the virtual environment.

6. The method of claim 1, wherein the behavioral data comprises at least one of:
   gait data;
   posture data;
   facial expression data;
   speech data;
   mobility data;
   reaction data; or
   accuracy data.

7. The method of claim 1, wherein the extracting the behavioral data comprises detecting an acute health event via at least one second detection model.

8. The method of claim 7, wherein the detecting the at least one health anomaly related to the physical condition of the user comprises determining that the acute health event is associated with the physical condition of the user.

9. The method of claim 8, wherein the determining that the acute health event is associated with the physical condition of the user comprises determining that the acute health event is not a virtual event related to the virtual representation of the user within the virtual environment.

10. The method of claim 1, wherein the detecting the at least one health anomaly related to the physical condition of the user comprises:
    applying at least a portion of the behavioral data to the at least one first detection model;
    obtaining an indication of the at least one health anomaly as an output of the at least one first detection model; and
    determining that the at least one health anomaly is related to the physical condition of the user in response to the obtaining of the indication of the at least one health anomaly as the output of the at least one first detection model.

11. The method of claim 1, wherein the detecting the at least one health anomaly related to the physical condition of the user comprises:
    verifying that the at least one health anomaly is related to the physical condition of the user via biometric data of the user.

12. The method of claim 11, wherein the biometric data of the user comprises an additional input to the at least one first detection model.

13. The method of claim 1, wherein the alert is provided to at least one of:
- an endpoint device of the user that is used to access the virtual environment;
- a medical entity designated by the user or that is assigned to a location associated with the user; or
- a caregiver designated by the user.

14. The method of claim 1, wherein the avatar comprises an anthropomorphized animal or an object.

15. The method of claim 1, wherein the processing system is for detecting health anomalies from different instances of behavioral data associated with at least one virtual representation of the user extracted from different visual data feeds of a plurality of different virtual environments.

16. A method comprising:
- obtaining, by a processing system including at least one processor, a visual data feed of a region of a virtual environment associated with a virtual representation of a user within the virtual environment, wherein the virtual representation of the user comprises an avatar;
- extracting, by the processing system, behavioral data of the virtual representation of the user from the visual data feed;
- detecting, by the processing system, at least one health anomaly related to a physical condition of the user from the behavioral data via at least one first detection model for detecting the at least one health anomaly, wherein the at least one first detection model comprises at least one machine learning model; and
- generating, by the processing system, an alert in response to the detecting of the at least one health anomaly that is related to the physical condition of the user.

17. An apparatus comprising:
- a processing system including at least one processor; and
- a computer-readable medium storing instructions which, when executed by the processing system, cause the processing system to perform operations, the operations comprising:
  - obtaining a visual data feed of a region of a virtual environment associated with a virtual representation of a user within the virtual environment, wherein the virtual representation of the user comprises an avatar;
  - extracting behavioral data of the virtual representation of the user from the visual data feed;
  - detecting at least one health anomaly related to a physical condition of the user from the behavioral data via at least one first detection model for detecting the at least one health anomaly, wherein the at least one first detection model comprises at least one machine learning model; and
  - generating an alert in response to the detecting of the at least one health anomaly that is related to the physical condition of the user.

18. The apparatus of claim 17, wherein the processing system is a processing system of an endpoint device of the user that is used to access the virtual environment.

19. The apparatus of claim 17, wherein the processing system comprises a processing system of a server hosting the virtual environment, wherein the operations are performed via at least one first process that is distinct from at least one second process that is for hosting the virtual environment.

20. The apparatus of claim 19, wherein the at least one second process provides the visual data feed of the region of the virtual environment.

* * * * *